(12) United States Patent
Fischer, Jr.

(10) Patent No.: US 8,057,496 B2
(45) Date of Patent: Nov. 15, 2011

(54) MECHANICAL THROMBECTOMY DEVICE

(75) Inventor: Frank J. Fischer, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 379 days.

(21) Appl. No.: 12/245,807

(22) Filed: Oct. 6, 2008

(65) Prior Publication Data

US 2010/0087844 A1 Apr. 8, 2010

(51) Int. Cl.
*A61B 17/22* (2006.01)

(52) U.S. Cl. ..................................... 606/159; 604/508

(58) Field of Classification Search .......... 606/127–128, 606/159, 200; 604/508
See application file for complete search history.

(56) References Cited

U.S. PATENT DOCUMENTS

| | | | |
|---|---|---|---|
| 5,064,428 A | 11/1991 | Cope et al. | |
| 5,330,482 A | 7/1994 | Gibbs et al. | |
| 5,370,653 A | 12/1994 | Cragg | |
| 5,476,450 A * | 12/1995 | Ruggio | 604/28 |
| 5,498,236 A | 3/1996 | Dubrul et al. | |
| 5,630,823 A | 5/1997 | Schmitz-Rode et al. | |
| 5,893,869 A | 4/1999 | Barnhart et al. | |
| 6,030,397 A | 2/2000 | Monetti et al. | |
| 6,203,552 B1 | 3/2001 | Bagley et al. | |
| 6,322,572 B1 | 11/2001 | Lee | |
| 6,635,027 B1 | 10/2003 | Cragg et al. | |
| 6,652,548 B2 | 11/2003 | Evans et al. | |
| 6,852,097 B1 | 2/2005 | Fulton, III | |
| 6,929,633 B2 | 8/2005 | Evans et al. | |
| 6,936,025 B1 | 8/2005 | Evans et al. | |
| 7,101,380 B2 * | 9/2006 | Khachin et al. | 606/127 |
| 2002/0058904 A1 | 5/2002 | Boock et al. | |
| 2005/0043756 A1* | 2/2005 | Lavelle et al. | 606/200 |
| 2005/0277979 A1 | 12/2005 | Dorros et al. | |
| 2006/0253145 A1 | 11/2006 | Lucas | |
| 2007/0161963 A1 | 7/2007 | Smalling | |
| 2007/0260266 A1 | 11/2007 | Karpiel | |

OTHER PUBLICATIONS

"Evidence-Based Instrumentation for Flexible Ureteroscopy: A Revew," by Timothy Holden et al., Journal of Endourology, vol. 22, No. 7, Jul. 2008, 4 pgs.

* cited by examiner

*Primary Examiner* — Victor Nguyen
(74) *Attorney, Agent, or Firm* — Brinks Hofer Gilson & Lione

(57) ABSTRACT

A medical device for removing a thrombus from a blood vessel and a process thereof is presented. The device includes an outer sheath with a plurality of lumens. A wire guide inserted through one of the lumens is used to place the device proximate to a thrombus. A chemical lysing agent is used to at least partially lyse the thrombus. A wire basket extended through the first lumen proximate to the thrombus is translated back and forth to generate a force that may be transmitted to the partially lysed thrombus assisting in the formation of smaller fragments. A vacuum coupled to the distal end of the second lumen is used to remove the lysed thrombus fragments.

6 Claims, 4 Drawing Sheets

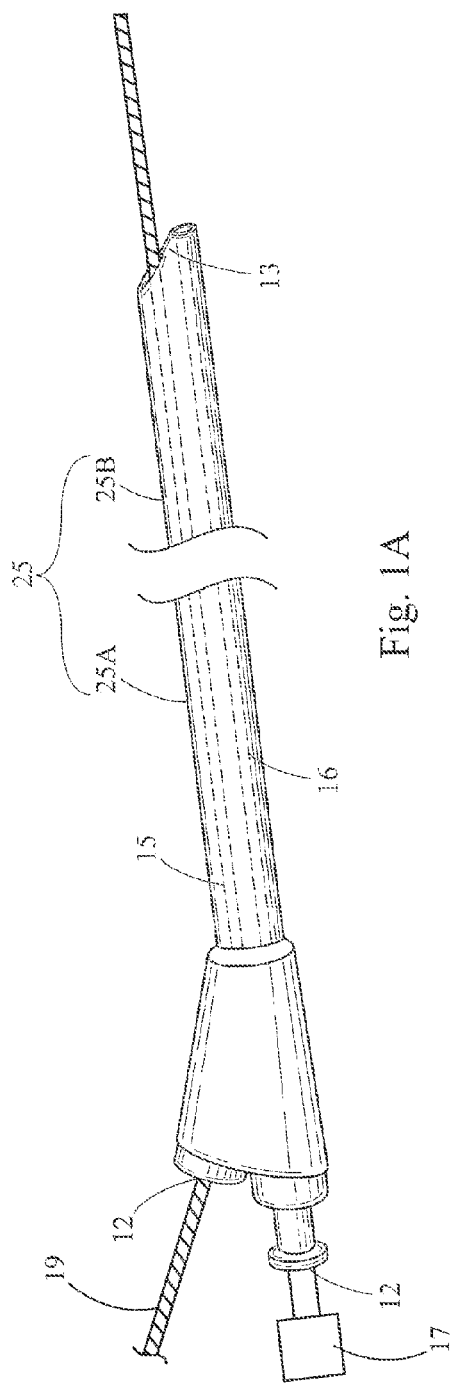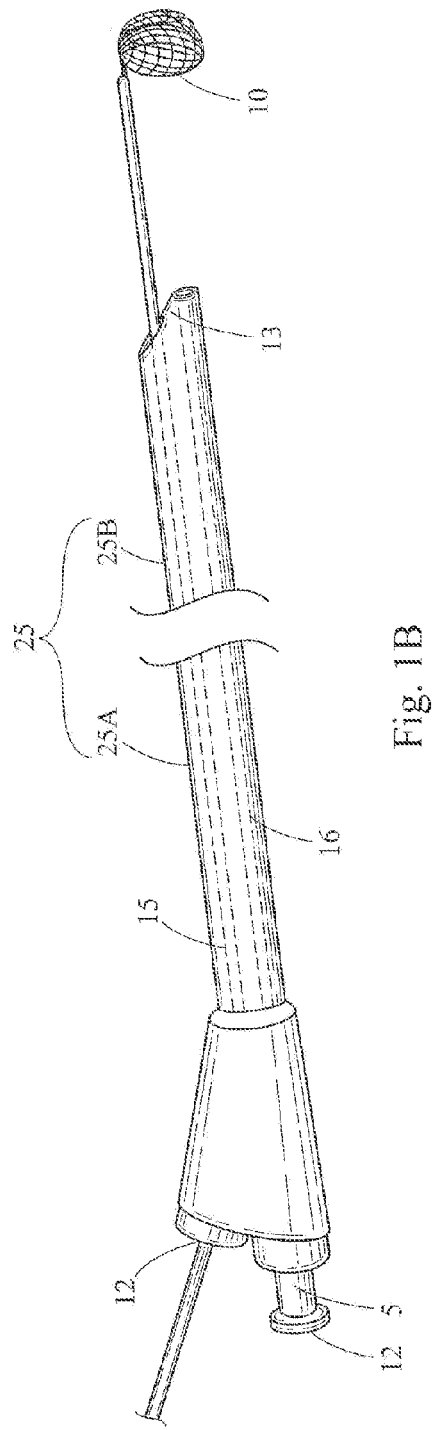

MECHANICAL THROMBECTOMY DEVICE

FIELD

This invention relates to medical devices, and more particularly, to devices used to remove thrombus or soft tissue clots from vascular or other lumens.

BACKGROUND

Vascular disease affects a large proportion of individuals each year. One indication of the existence of this disease is the development of a blood clot in the vascular system, which if left untreated may result in deep venous thrombosis, embolisms, or ischemia. These clots, which may either partially or fully occlude a vessel, are usually comprised of an aggregated mixture of thrombus and fibrin.

Various known techniques for the removal of blood clots include both chemical and mechanical treatment. Chemical treatment typically involves the injection of lysing agents into the vessel near the blood clot to chemically attack, dissolve, and disperse the occlusion. In this technique, the lysing agent is brought into the proximate vicinity of the blood clot via injection through a cannula or other lumen.

The mechanical treatment of a blood clot typically involves the use of catheters having a rotary cutting head or other form of a rotor/stator homogenizing head. Examples of such rotary devices include rotating burr devices, rotating a helical coil wire within a catheter, and recanalization catheters. Other mechanical devices utilize a sharp point to methodically pummel the occlusion in order to form a hole through it. In each of these cases, although the occlusion is reduced in size or a passageway is created, the residual thrombus/fibrin material resulting from the treatment remains within the vessel.

The removal of residual material formed during the fragmentation of a blood clot is medically desirable. It is further necessary to insure that this residual material does not migrate away from the site of the treatment to other parts of the vessel. Such migration could lead to serious complications, such as embolism, stroke, or a heart attack. The use of a vena cava filter has been employed to catch residual fragments that have migrated from the site of a blood clot. In addition, some mechanical devices have utilized the concept of aspiration to establish or maintain a flow rate through a catheter for the removal of residual thrombus/fibrin material during treatment.

Therefore, there is a need to create a medical device in which the elements of the device used to clear an occlusion enhances the ability of the device to effectively remove residual material or thrombus fragments from the vessel.

SUMMARY

The present invention generally provides a medical device for the removal of a thrombus from a blood vessel. In one embodiment, the medical device comprises a tubular outer sheath having a first lumen and a second lumen; a wire guide disposed through the distal end of the first lumen for delivery of the device into the patient; an injector mechanism causing a lysing agent to flow through the second lumen; a wire basket slidably received within the first lumen to generate a force that may cause further fragmentation of the partially lysed thrombus; and a vacuum port coupled to the distal end of the second lumen for removing lysed thrombus fragments. The proximal ends of the first and second lumen are positioned proximate to the thrombus with the device being operable in two modes, which include a first delivery mode and a second mixing mode. In the first delivery mode, the basket is sized and extended proximate to the thrombus. In the second mixing mode, the basket is caused to engage the thrombus to transmit force thereto in the furtherance of lysing, fragmenting, and removing the thrombus.

In another aspect of the present invention, the lysing agent is an antibody selected as one from the group of streptokinase, urokinase, plasmin, alteplase, tenecteplase, reteplase, and a tissue plasminogen activator. In addition, if desirable, the lysing agent may further comprise surface active polymers, emulsifying agents, anticoagulants, or a mixture thereof. The lysing agent may be delivered to the thrombus as part of an isotonic or iso-osmotic solution.

In another aspect of the present invention, the wire basket is formed into either an umbrella-shape or helical shape being comprised of at least three wires. The wire basket may be coupled to a control member that can be used by an operator to manipulate the wire basket. The wire basket is collapsible and can fit within a sheath or the first lumen of the medical device.

It is another objective of the present invention to provide a method of removing a thrombus from a blood vessel. This method comprises the steps of introducing a sheath having a first lumen and a second lumen into a blood vessel; inserting a wire guide through the first lumen; positioning the proximal end of the first lumen and second lumen proximate to a thrombus; injecting a lysing agent into the blood vessel through the second lumen to at least partially lyse or dissolve the thrombus; delivering a cannula through the first lumen proximate to the thrombus; removing the wire guide from the first lumen; extending a wire basket from the first lumen to a position proximate to the thrombus; causing the wire basket to translate back and forth to generate a force; transmitting the force from the basket to the thrombus to break the partially lysed thrombus into smaller fragments; applying a vacuum to the second lumen through the port positioned near the distal end of the first lumen; and removing the partially lysed thrombus fragments via the applied vacuum.

In another aspect of the present invention, the method further comprises the step of securing the thrombus fragments proximate to the wire basket after lysing and further fragmentation of the thrombus has occurred.

In yet another aspect of the present invention, the step of injecting a lysing agent into the blood vessel enhances the blood flow in the narrow passage ways in and around the thrombus and increases the ability of the lysing agent to be delivered to the thrombus. The lysing agent may activate fibrinolysis, thereby, affecting the cross-linking or polymerization of fibrinogen and reducing the stability of the thrombus.

In yet another aspect of the present invention, the operator may control the wire basket relative to the sheath by manipulating it using a control member. The wire basket preferably has at least one of its wires slidably receivable within a sheath and is collapsible within the sheath in order to be delivered proximate to the partially lysed thrombus.

In another aspect, in addition to removing lysed thrombus fragments, the application of a vacuum may also hold the lysed thrombus in a position that is proximate to the proximal end of the second and first lumen.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present invention in any way.

FIG. 1 is perspective view of a thrombectomy device in accordance with one embodiment of the present invention.

DETAILED DESCRIPTION

Figure 2A:
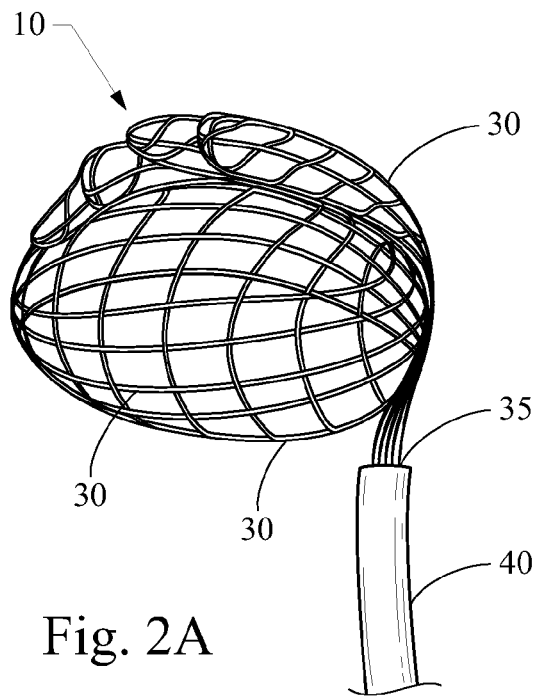
FIG. 2A is an enlarged view of the wire basket of the thrombectomy device in accordance with one embodiment of the present invention.

The following description is merely exemplary in nature and is in no way intended to limit the present disclosure or its application or uses. It should be understood that throughout the description and drawings, corresponding reference numerals indicate like or corresponding parts and features.

The present invention provides a medical device useful for the removal of a thrombus from a blood vessel. Referring to FIGS. 1A-B, this medical device 1 comprises a flexible tubular outer sheath 25 that encloses both a first lumen 15 and a second lumen 16 with each lumen having a distal portion 25B extending to a distal end 13 and a proximal portion 25A extending from the distal portion 25B to a proximal end 12.

Referring now to FIG. 1A, a wire guide 19 is placed through the proximal end 12 of the first lumen 15 to the distal end 13 of the first lumen 15 for delivery into the patient and positioning of the first and second lumens proximate to the thrombus. A lysing agent is injected through the second lumen 16 to the thrombus by the action of an injector mechanism 17. The wire guide is removed and a wire basket 10 is extended through the distal end 13 of the first lumen 15 to a position that is beyond the thrombus. As shown in FIG. 1B, the wire basket 10 is slidably received by the first lumen 15 in order to generate and transmit a force to the partially lysed thrombus that may assist in breaking it into smaller fragments. A vacuum port 5 is coupled to the proximal portion 25A of the second lumen 16 for removal of thrombus fragments formed after lysing and fragmentation of the thrombus has occurred. During the operation of the thrombectomy device 1, the distal ends 13 of the first 15 lumen and second 16 lumen are positioned proximate to the thrombus.

The wire guide arrangement in the first lumen 15 includes the use of a hollow needle (not shown) to pierce the patient's skin and enter the body tissue at an angle with respect thereto. A wire guide 19 is then inserted into the hollow needle and is advanced percutaneously into the body tissue to a desired position proximate to the occlusion in the vessel. The hollow needle is then pulled in a backward direction so as to be removed from the body tissue and from contact with the wire guide 19. Next, the thrombectomy device 1 through its first lumen 15 is advanced along the wire guide 19 to a desired position proximate to the thrombus.

A chemical lysing agent refers to any substance known to one skilled in the art, including but not limited to enzymes and antibodies, that subjects a thrombus to a mechanism, such as lysis, cytolysis, or fibrinolysis, among others, which results in at least the partial dissolution, fragmentation, destruction, decomposition, or break-up of said thrombus. Examples of an enzyme or antibody that may be used as a lysing agent include, but not limited to streptokinase, urokinase, plasmin, alteplase, tenecteplase, reteplase, or a tissue plasminogen activator. The lysing agent preferably activates fibrinolysis, which affects the cross-linking or polymerization of fibrinogen, thereby reducing the stability of a thrombus and resulting in its partial dissolution. The concentration of the chemical lysing agent used is predetermined based upon the amount necessary to partially or fully lyse the size of the thrombus encountered. The chemical composition of the lysing agent may enhance the blood flow in the narrow passage ways in and around the fibrin-thrombus obstruction, thereby, increasing the ability of the lysing agent to be delivered to the thrombus. One skilled in the art will recognize that the lysing agent may further include effective concentrations of surface active polymers, emulsifying agents, anticoagulants, and other additives useful in either increasing the solubility of the lysing agent in water/blood, assisting in the dissolution of the thrombus, or inhibiting the re-growth of the thrombus.

Preferably the lysing agent is delivered as part of an isotonic or iso-osmotic solution, which is at the same or similar osmotic pressure as the blood within the obstructed vessel. Examples of solutions in which the lysing agent may be incorporated include saline, Ringer's solution, Krebs-Ringer's solution, and lactated Ringer's solution, among others. It should be understood that the lysing agent may also be delivered in a solution that is not isotonic in nature.

Figure 2B:
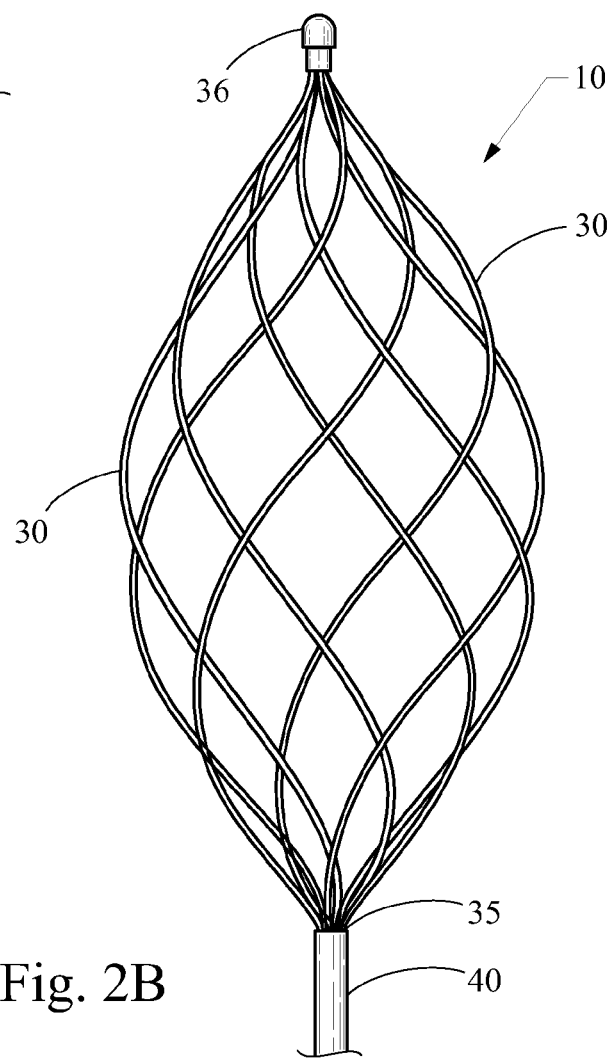
FIG. 2B is an enlarged view of the wire basket of the thrombectomy device in accordance with another embodiment of the present invention.

Referring now to FIGS. 2A and 2B, the wire basket 10 may be formed by distal portions of a plurality of multifilament wires 30 joined at a first location 35 to a control member 40. It is feasible that the control member 40 be formed by twisting the multifilament wires 30 together or formed as a separate member, such as a rod. The control member 40 extends proximally through the first lumen. The wires may be twisted to be in contact with one another or joined by soldering, welding, use of metal bands, or clamps. It is feasible that the wires may form a second joint 36 at a distal tip that is shaped autraumatically to help prevent the occurrence of any damage to the vessel.

Preferably the wire basket 10 so formed is umbrella-shaped (FIG. 2A) or helical shaped (FIG. 2B), although other shapes could be utilized. The wire basket 10 is preferably comprised of at least three wires 30. At least one of the wires 30 and preferably all of the wires are slidably receivable within a sheath (not shown). The wires may have any cross-sectional shape known to one skilled in the art, with wedge-shaped or pie-shaped in its cross-section representing two examples. Each wire preferably has a diameter of about 0.013 inches and may be comprised of multi-filaments with each filament having a cross-sectional diameter smaller than about 0.013 inches.

The wires may be composed of any medical grade material having the flexibility and strength necessary to be delivered to the obstructed site within a vessel and used to break-up a partially lysed thrombus into smaller fragments. Examples of appropriate medical grade materials, include, but are not limited to stainless steel and nitinol.

The wire basket 10 is preferably delivered through the first lumen 15 of the medical device 1 using a delivery cannula or sheath (not shown). Manipulation of the control member 40 relative to the delivery sheath provides the operator with control over the wire basket 10. The wires when collapsed inside a sheath or cannula assume an approximately cylindrical shape in order to substantially fill the cross-sectional area of the sheath. Once the sheath and wire basket are delivered to a position that is proximate to the partially lysed thrombus, the sheath is retracted or the control member further extended, resulting in the wire basket becoming exposed and allowed to expand to its desired shape.

Figure 3:
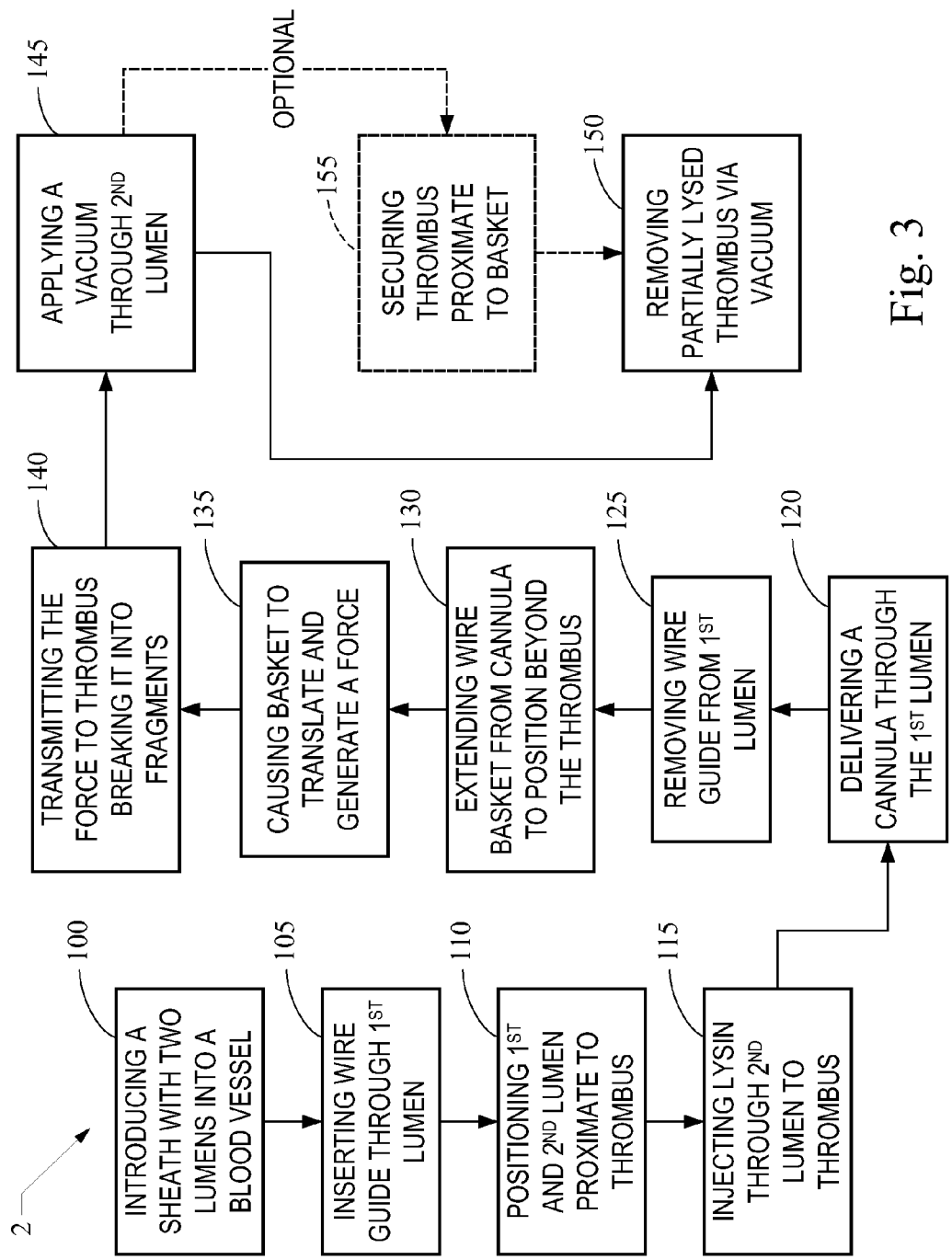
FIG. 3 is a schematic representation of a method for removing a thrombus from a vessel according to one embodiment of the present invention.

It is another objective of the present invention to provide a method 2 for removing a thrombus from a blood vessel. Referring now to FIG. 3, this method comprises the steps of introducing 100 a sheath having a first lumen and a second lumen into a blood vessel; inserting 105 a wire guide through the first lumen; positioning 110 the proximal end of the first and second lumen proximate to a thrombus; injecting 115 a lysing agent through the $2^{nd}$ lumen to the thrombus to at least partially lyse or dissolve the thrombus; delivering 120 a cannula through the $1^{st}$ lumen; removing 125 the wire guide from the $1^{st}$ lumen; extending 130 a wire basket through the distal end of the cannula to a position that is proximate to the thrombus; causing 135 the basket to translate back and forth to generate a force; transmitting 140 the force from the basket to the thrombus to break the partially lysed thrombus into smaller fragments and to assist in lysing; applying a vacuum 145 to the second lumen through a port positioned near the distal end of the second lumen; and removing 150 the residual material via the applied vacuum.

The method of removing a thrombus from a blood vessel may further comprise the step of securing 140 the partially lysed and dissolved thrombus fragments proximate to the wire basket prior to their removal 150 by the vacuum. This optional step provides additional assurance that thrombus fragments do not migrate away from the site of the treatment to other parts of the vessel where they may potentially lead to serious complications, such as embolism, stroke, or a heart attack.

Figure 4:
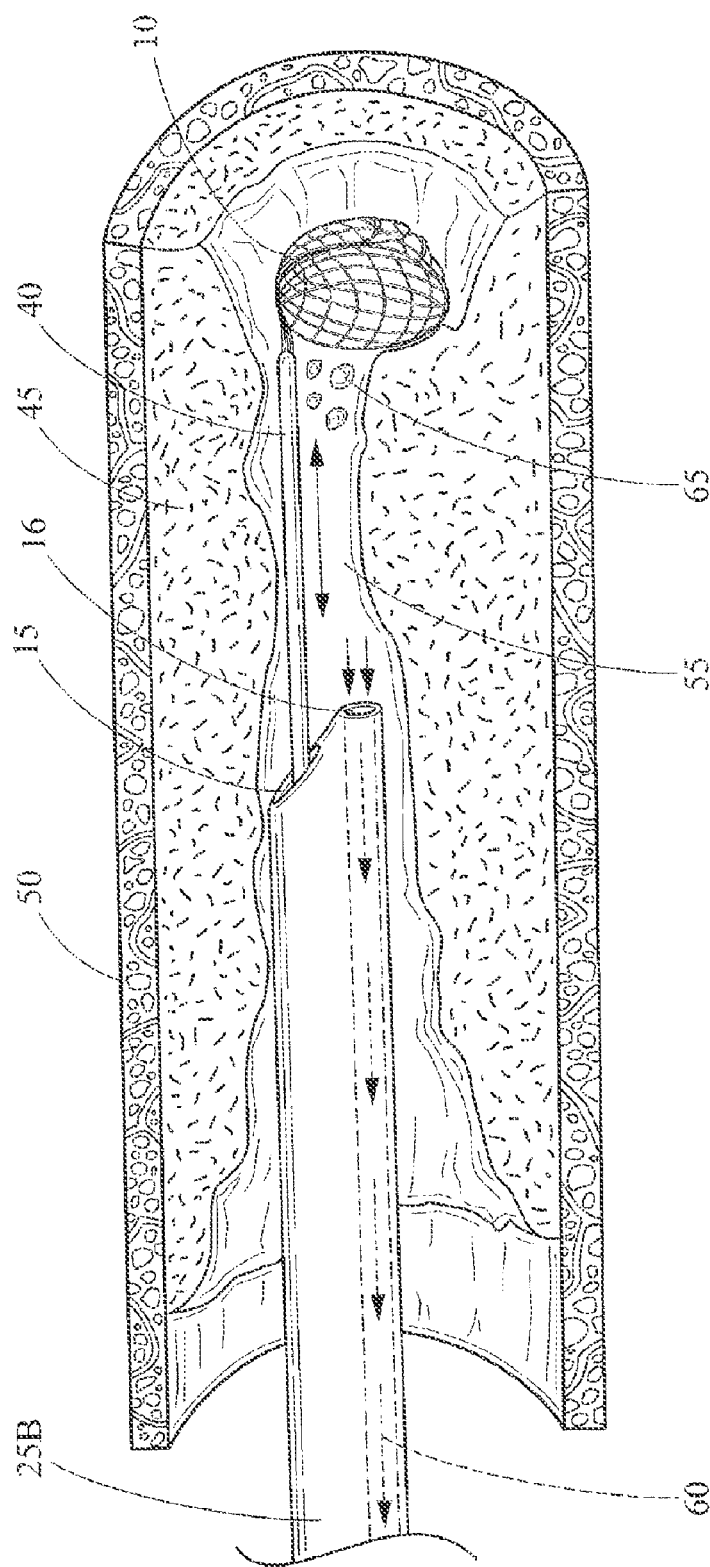
FIG. 4 is a schematic view of the distal portion of a thrombectomy device engaged in the removal of a thrombus present in a vessel in accordance with one embodiment of the present invention.

Referring now to FIG. 4, an example in which the distal portion 25B of a thrombectomy device engaged in an interaction with a thrombus 45 located within a blood vessel 50 is depicted. A wire guide is used to bring the first 15 and second 16 lumen near or proximate to the thrombus 45. Lysing agent 55 is injected through the second lumen 16 to at least partially lyse the thrombus 45. A wire basket 10 is then extended through a sheath (not shown) from the first lumen 15 via manipulation using a control member 40. Translation of the wire basket 10 back and forth generates a force that is transmitted to the thrombus 45, thereby, facilitating breaking the partially lysed thrombus into smaller fragments 65. A vacuum 60 applied through the second lumen 16 assists in the removal of the partially lysed thrombus fragments 65.

In addition to removing partially lysed thrombus fragments, the application of a vacuum 60 may also hold the thrombus 45 in a position at the proximal end of the proximal portion of the second lumen 16, which may effectively assist the chemical dissolution and mechanical fragmentation process.

A person skilled in the art will recognize from the previous description that modifications and changes can be made to the present disclosure without departing from the scope of the disclosure as defined in the following claims.

What is claimed is:

1. A medical device to partially lyse and remove a thrombus from a blood vessel, the device comprising:
   a tubular outer sheath having a first lumen and a second lumen with each lumen having a distal portion extending to a distal end and a proximal portion extending from the distal portion to a proximal end;
   a wire guide placed into the proximal end of the first lumen for delivery to a patient through the proximal end of the first lumen,
   an injector mechanism causing a lysing agent to flow through the second lumen; and
   a wire basket slidably received within the first lumen to replace the wire guide, the wire basket having a proximal end and a distal tip and comprising a plurality of wires, the plurality of wires extending helically from the proximal end to the distal tip;
   a vacuum applied through the second lumen to remove the at least partially lysed thrombus;
   the device being operable in two modes including a first delivery mode and a second mixing mode;
   wherein the wire basket is sized and extended proximate to the thrombus in said delivery mode;
   wherein the wire basket is caused to engage the thrombus to transmit force thereto in the furtherance of at least partially lysing and removing the thrombus in said mixing mode;
   wherein the wire basket is coupled to a control member that may be used by an operator to manipulate the wire basket;
   wherein the wire basket is collapsible and fits within the first lumen.

2. The device of claim 1, wherein the lysing agent is an antibody selected as one from a group of streptokinase, urokinase, plasmin, alteplase, tenecteplase, reteplase, and a tissue plasminogen activator.

3. The device of claim 1, wherein the lysing agent further comprises surface active polymers, emulsifying agents, anticoagulants, or a mixture thereof.

4. The device of claim 1, wherein the lysing agent is delivered as part of an isotonic or iso-osmotic solution.

5. The device of claim 4, wherein the isotonic solution is one selected from a group of saline, Ringer's solution, Krebs-Ringer's solution, and lactated Ringer's solution.

6. The device of claim 1, wherein the wire basket is comprised of at least three wires.

* * * * *